United States Patent
Sollmann

(10) Patent No.: US 9,040,437 B2
(45) Date of Patent: May 26, 2015

(54) ELASTIC LAMINATE

(75) Inventor: Henner Sollmann, Gronau (DE)

(73) Assignee: MONDI CONSUMER PACKAGING TECHNOLOGIES GMBH, Gronau (DE)

( * ) Notice: Subject to any disclaimer, the term of this patent is extended or adjusted under 35 U.S.C. 154(b) by 242 days.

(21) Appl. No.: 12/972,655

(22) Filed: Dec. 20, 2010

(65) Prior Publication Data

US 2012/0003421 A1   Jan. 5, 2012

(30) Foreign Application Priority Data

Dec. 19, 2009  (EP) ..................... 09015760

(51) Int. Cl.
| | | |
|---|---|---|
| *B32B 7/04* | (2006.01) | |
| *B32B 7/02* | (2006.01) | |
| *A61F 13/49* | (2006.01) | |
| *A61F 13/56* | (2006.01) | |
| *B32B 5/26* | (2006.01) | |
| *B32B 27/12* | (2006.01) | |

(52) U.S. Cl.
CPC .............. *B32B 7/02* (2013.01); *Y10T 428/265* (2013.01); *Y10T 428/24975* (2013.01); *Y10T 428/24273* (2013.01); *A61F 13/4902* (2013.01); *A61F 13/56* (2013.01); *B32B 5/26* (2013.01); *B32B 7/04* (2013.01); *B32B 27/12* (2013.01)

(58) Field of Classification Search
CPC .............. B32B 5/26; B32B 7/02; B32B 7/04; B32B 7/12; B32B 27/12; A61F 3/56; A61F 13/4902
USPC .................................... 442/149, 327
See application file for complete search history.

(56) References Cited

U.S. PATENT DOCUMENTS

| | | | |
|---|---|---|---|
| 6,159,584 A | 12/2000 | Eaton | |
| 6,531,207 B1 | 3/2003 | Eaton | |
| 8,741,083 B2 | 6/2014 | Wennerbaeck | |
| 2003/0105446 A1 | 6/2003 | Hutson et al. | |
| 2003/0183316 A1* | 10/2003 | Hamulski | 156/73.1 |
| 2004/0044324 A1 | 3/2004 | Swenson et al. | |
| 2005/0130543 A1* | 6/2005 | Baldauf | 442/394 |
| 2006/0162843 A1* | 7/2006 | Baldauf et al. | 156/73.1 |
| 2007/0237924 A1 | 10/2007 | Bruce et al. | |
| 2008/0038983 A1* | 2/2008 | Hagemann et al. | 442/396 |
| 2010/0104830 A1 | 4/2010 | Jaeger et al. | |

FOREIGN PATENT DOCUMENTS

WO    WO 2007133128 A1 * 11/2007

* cited by examiner

*Primary Examiner* — Peter Y Choi
(74) *Attorney, Agent, or Firm* — Andrew Wilford

(57) ABSTRACT

An elastic laminate has a coextruded film having an outer film layer formed of an elastic and sticky styrene-block copolymer and an inner film layer of lesser elasticity than the outer layer, an outer fleece or nonwoven web or overlay, an outer adhesive layer between the outer fleece web and the outer film layer adhering the outer fleece web to the outer film layer, an inner fleece or nonwoven web or overlay, and an inner adhesive layer between the inner fleece web and the inner film layer adhering the inner fleece web to the inner film layer. The inner adhesive layer forming between the inner fleece web and the inner film layer a bond that is weaker than a bond formed by the outer adhesive layer between the outer fleece web and the outer film layer such that on stretching the inner fleece layer separates locally from the inner film layer.

10 Claims, 1 Drawing Sheet

ELASTIC LAMINATE

FIELD OF THE INVENTION

The present invention relates to an elastic laminate.

BACKGROUND OF THE INVENTION

An elastic laminate is known having a film on both its faces by monolayer or multilayer nonwoven overlays. The elastic laminate is provided in particular for parts of hygiene articles subject to high stresses, such as elastic closing strips on disposable diapers, for example.

Styrene block copolymers are characterized by good elastic properties and are therefore suitable for producing elastic laminates that are subject to high stresses.

Because of the very high elasticity, styrene block copolymers are very sticky and can therefore be processed as monofilaments only with great effort. In addition to an elongation that is difficult to control during processing of such a film, it cannot easily be rolled up into a roll because then there is an increased risk of sticking together.

DE 298 25 018 (U.S. Pat. Nos. 6,159,584 and 6,531,207) describes a stretchable elastic strip having a coextruded elastic film. The elastic film comprises an elastic layer as well as at least one additional inelastic layer. In the case of the stretchable elastic strip, the coextruded film is covered by a nonwoven overlay on at least one face, producing stretchable and unstretchable regions in specific zones. It is possible to provide here for the nonwoven overlay to be connected to the coextruded film in fastening regions that are spaced apart from one another in the stretchable regions, thereby forming raised arched regions between the fastening regions. Due to the alternation between defined fastening regions and arched regions, this forms a definitely perceptible and recognizable wave shape that impairs the feel and the textile character of the material.

OBJECTS OF THE INVENTION

It is therefore an object of the present invention to is provide an improved elastic laminate.

Another object is the provision of such an improved elastic laminate that overcomes the above-given disadvantages, in particular that has a uniform surface that is especially soft on one face.

SUMMARY OF THE INVENTION

An elastic laminate has according to the invention a coextruded film having an outer film layer formed of an elastic and sticky styrene-block copolymer and an inner film layer of lesser elasticity than the outer layer, an outer fleece or nonwoven web or overlay, an outer adhesive layer between the outer fleece web and the outer film layer adhering the outer fleece web to the outer film layer, an inner fleece or nonwoven web or overlay, and an inner adhesive layer between the inner fleece web and the inner film layer adhering the inner fleece web to the inner film layer. The inner adhesive layer forming between the inner fleece web and the inner film layer a bond that is weaker than a bond formed by the outer adhesive layer between the outer fleece web and the outer film layer such that on stretching the inner fleece layer separates locally from the inner film layer.

The inner and outer adhesive layers are applied as continuous layers covering the entire confronting faces of the respective film layers and fleece webs. But since the inner adhesive has a weaker bond, if the laminate is stretched there will be local separation between the inner film layer and the inner fleece web and inelastic stretching of the inner web so that when the stretching tension is released, there will be bunching of the inner fleece web to form a very soft and continuous inner surface on the laminate. These local separations can be between the inner fleece layer and the inner adhesive layer, or between the inner film layer and the inner adhesive layer.

Before such activation by stretching, both the outer fleece web on the outer film layer and the inner nonwoven overlay web having the inner film layer are joined over the full region by the respective adhesive layer. The adhesion is adjusted so that in activation by an initial stretching, the inner film layer is separated from the inner adhesive layer and/or the outer film layer in some regions. The adhesion between the inner film layer and the inner adhesive layer is usually also lower than the cohesive bonding forces within the inner adhesive layer and is also lower than the adhesion between the adhesive layers on the one hand and the respective nonwoven overlay on the other hand. Then in the elongation an adhesion failure occurs between the inner film layer and the outer film layer and/or the inner film layer and the inner adhesive layer. Due to the separation occurring in some layers within the layer composite, a microstructure without a fixed pattern is created, resulting in minor warping distributed over the entire region of the elastic laminate under the inner nonwoven overlay, thereby improving the haptic properties of the inner nonwoven overlay. Thus, in comparison with a design in which there is no separation of layers in some regions, a softer, more voluminous surface is created with the same weight per unit of region of the inner nonwoven overlay.

The nonwoven overlay web may also be formed by one layer or multiple layers of a carded nonwoven, a spunbond nonwoven or a melt-blown nonwoven, and multilayer combinations of different nonwoven materials may also be considered in particular. Polyolefins such as polyethylene or polypropylene, polyolefin copolymers or polyolefin blends are preferred as the basic substance of the fibers because of the low cost for disposable items in particular.

The present invention is based on the discovery that, by adjusting the adhesion at the interfaces of the inner film layer, the feel or hand can be improved for the inner nonwoven overlay. The layer separation according to the invention may also be accomplished by suitably coordinating the polarities of the individual layers, but in general, great differences in polarity lead to a reduction in adhesion. The styrene block copolymer as a material for the outer film layer has a moderate polarity. In addition, according to a preferred embodiment of the invention, a hot-melt adhesive based on styrene block copolymer, in particular styrene-isoprene-styrene block copolymer (SIS), is used as the material for the adhesive layers, such that basically both adhesive layers may be formed from the same adhesive. In addition, adhesives based on polyurethane (PU) may also be used. To achieve local adhesion failure in some regions on one of the interfaces of the inner film layer, a material that definitely differs in polarity from the adjacent layers is advantageously selected. Since the styrene block copolymers have a moderate polarity, either strongly polar polymers and polymers having a low polarity or apolar polymers are suitable for the inner film layer.

Suitable polymers having a strong polarity include, for example, polyamides (PA) with their strongly polar amide group, polymethyl methacrylate (PMMA), polyoxymethylene (POM) and ester thermoplastics, such as polycarbonate (PC), polyethylene terephthalate (PET) and polybutylene terephthalate (PBT). In addition, at least two of the above-described polymers and/or different types of the above-described polymers may also be provided as a mixture.

Depending on the layer composition, the desired separation may also be achieved with a moderately polar polymer in combination with an adjacent layer of a polymer that is apolar or has a low polarity. For example, polystyrene (PS), whose moderate polarity can be attributed to the p-electron system of the aromatic constituents, still has a high enough polarity, depending on the material combination.

Materials having a low polarity or none at all include in particular polyolefins, such as polyethylene (PE) and polypropylene (PP).

The polymers are selected so that the polarity difference between the outer film layer and the outer adhesive layer is lower than the polarity difference between the outer film layer and the inner film layer, on the one hand, and the polarity difference between the inner film layer and the inner adhesive layer, on the other hand.

The internal structure of the laminate after activation depends in particular on the material properties of the inner film layer and the type of activation process. An elongation of at least 50% usually occurs in activation, but an elongation of at least 100% is preferred, and a much greater increase in length may also be provided. The activation may occur in only one direction to establish a preferred direction of elongation. In particular there is also the possibility of creating a material that is essentially stiff with moderate tensile forces perpendicular to the direction of activation.

According to a first additional embodiment, the film layer remains completely continuous and imperforate even after activation. Within the scope of such an embodiment, the inner film layer undergoes plastic deformation during the activation without tearing. A section-by-section separation of layers may take place with respect to the outer film layer as well as the inner film layer.

According to an alternative embodiment, the inner film layer has breaks that are formed when the inner film layer cannot withstand the tensile forces during activation and therefore tears. Since the inner film layer is supported and guided to a certain extent by the inner nonwoven overlay adjacent over the inner adhesive layer as well as by the outer film layer, microtears, which are usually distributed over the surface, occur without completely tearing the inner film layer.

The coextruded film that preferably has only two layers usually has a total thickness between 12 µm and 150 µm. The thickness of the outer elastic film layer is usually between 10 µm and 100 µm, preferably between 25 µm and 70 µm. The inner film layer usually has a thickness between 2 µm and 50 µm, preferably between 5 µm and 20 µm. In this context it should be taken into account that the elastic properties of the laminate are determined essentially by the outer elastic film layer and restrictions in elasticity due to the inner film layer should be avoided. In the case of an adequate strength of the inner film layer, it may also stabilize the coextruded film as an intermediate product during processing, such that a great elongation of the coextruded film can be avoided during handling of the coextruded film under tension. In particular a coextruded film may also be rolled up and stored as an intermediate product because the inner nontacky film layer as a separation between the layers of the outer film layer on top of one another prevents blocking.

The adhesion may be determined according to DIN 53357: 1982.

Strips may be cut from the elastic laminate and may be used to a particular extent as elastic closing strips on diapers.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
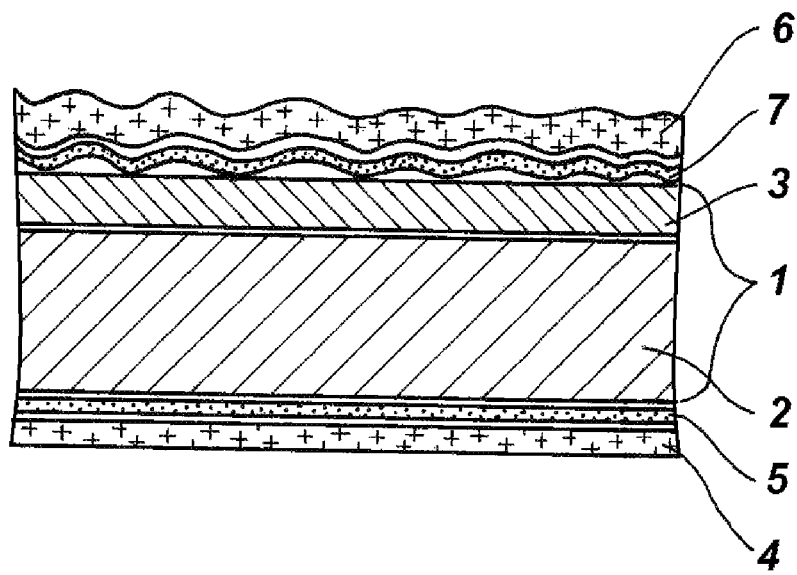
FIG. 1 is a large-scale section through the laminate according to the invention.

As seen in FIG. 1, an elastic laminate has a two-layer coextruded film 1 having an outer tacky film layer 2 of styrene block copolymer and an inner film layer 3 having a lower elasticity than the outer film layer 2. An outer fleece web 4 is bonded to the outer film layer 2 over the full region by an outer adhesive layer 5.

An inner adhesive layer 7 is arranged between the inner film layer 3 and an inner nonwoven overlay 6 and is detached from the inner film layer 3 in some regions but still adheres to it. This local separation is achieved by an initial elongation of the laminate with a 100% increase in length, for example. In the case of essentially complete restoration of the laminate, based on the elastic properties of the outer film layer 2, the material contracts again, such that the inner film layer 3 is separated from the inner adhesive layer 7 in some regions due to an adhesion failure because of the low adhesion at the joint interface. Due to the deformations of the inner nonwoven overlay 6 and the inner adhesive layer 7, the inner nonwoven overlay 6 becomes more voluminous on the whole without revealing a discernible macroscopic structure to a user. Instead, a pleasant feel is achieved even with a low weight per unit of region of the inner nonwoven overlay 6.

Figure 2:
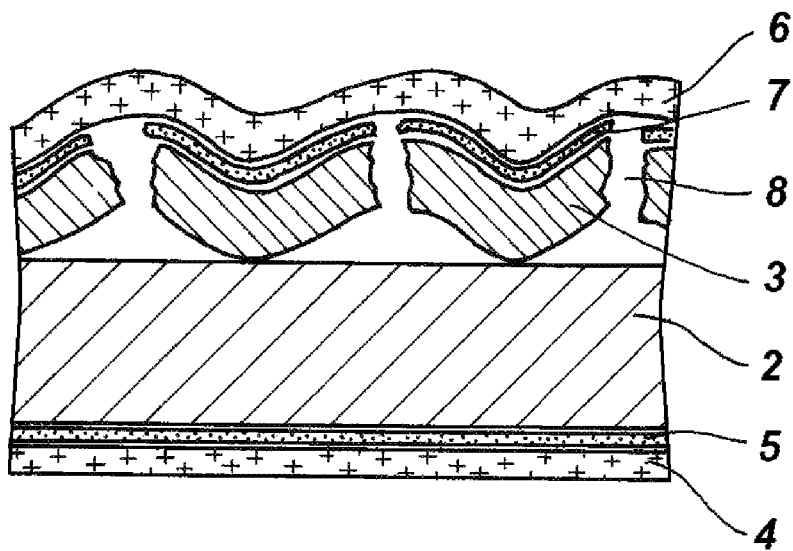
FIG. 2 is a view like FIG. 1 of another laminate in accordance with the invention.

FIG. 2 shows an embodiment having a basically comparable layer structure, where the material of the inner film layer is selected and the activation is performed in such a way that the inner film layer 3 tears in some regions, so that breaks 8 remain in the inner film layer 3 after the activation. In addition, the polarity of the inner film layer is coordinated with the material of the outer film layer in such a way that there is separation in some regions at the interface between the film layers 2 and 3. As described previously with respect to FIG. 1, the local separation produces a microstructuring below the inner nonwoven overlay 6, so that the latter gives a softer and more voluminous effect.

I claim:

1. An elastic laminate comprising:
 a coextruded film having an elastic outer film layer formed of a styrene-block copolymer and an inner film layer of lesser elasticity than the outer film layer and the inner film layer being made of a polyamide, polymethylmethacrylate, polyoxymethylene, polycarbonate, polyethylene terephthalate, or polybutylene terephthalate or mixtures thereof;
 an outer polyolefin fleece web;
 an outer adhesive layer extending continuously between the outer fleece web and the outer film layer, adhering the outer fleece web to the outer film layer, made of a hot-melt adhesive based on a styrene block copolymer, and bonding the outer fleece web and the outer film layer together continuously over full surface regions between the outer fleece web and the coextruded film;
 an inner polyolefin fleece web; and
 an inner adhesive layer extending continuously between the inner fleece web and the inner film layer, adhering to the inner fleece web over a full surface region thereof, made of a hot-melt adhesive based on a styrene block copolymer, and forming between the inner fleece web and the inner film layer a bond that is discontinuous and weaker than a bond formed by the outer adhesive layer between the outer fleece web and the outer film layer and that is created by an initial stretching that locally separates the inner fleece web and the inner adhesive layer from the inner film layer and creates a microstructure without a fixed pattern while leaving a multiplicity of separate local bonds between the inner fleece layer and the inner film layer, the inner film layer and the inner fleece web being separated and not bonded together at breaks by the inner adhesive layer between the local bonds.

2. The elastic laminate defined in claim 1 wherein the inner and outer adhesive layers are of the same polymer.

3. The elastic laminate defined in claim 1 wherein a polarity difference between outer film layer and the outer adhesive layer is less than the polarity difference between the inner film layer and the outer film layer and the polarity difference between the inner film layer and the inner adhesive layer.

4. The elastic laminate defined in claim 1 wherein the fleece webs are of substantially identical composition and properties.

5. The elastic laminate defined in claim 4 wherein the outer film layer has a thickness between 10 μm and 100 μm.

6. The elastic laminate defined in claim 5 wherein the inner film layer is has a thickness between 2 μm and 50 μm.

7. The elastic laminate defined in claim 1 wherein the coextruded film has only two layers.

8. The elastic laminate defined in claim 1 wherein the working temperatures of the polymers of the outer film layer, the inner film layer, and both the adhesive layers is between 180° C. and 260° C.

9. The elastic laminate defined in claim 1 wherein the inner film layer is imperforate and continuous.

10. The elastic laminate defined in claim 1 wherein the outer film layer is formed by the initial stretching with breaks forming throughgoing perforations.

\* \* \* \* \*